US008639014B2

(12) United States Patent
Fischer et al.

(10) Patent No.: US 8,639,014 B2
(45) Date of Patent: Jan. 28, 2014

(54) DEVICE AND METHOD TO EXTRACT A TISSUE SAMPLE

(75) Inventors: Daniel Fischer, Erlangen (DE); Thomas Mertelmeier, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 85 days.

(21) Appl. No.: 13/222,270

(22) Filed: Aug. 31, 2011

(65) Prior Publication Data

US 2012/0051620 A1 Mar. 1, 2012

(30) Foreign Application Priority Data

Aug. 31, 2010 (DE) ........................ 10 2010 035 924

(51) Int. Cl.
*G06K 9/00* (2006.01)

(52) U.S. Cl.
USPC ........................................................ 382/133

(58) Field of Classification Search
None
See application file for complete search history.

(56) References Cited

U.S. PATENT DOCUMENTS

| | | | | |
|---|---|---|---|---|
| 5,608,849 | A * | 3/1997 | King, Jr. | 345/419 |
| 6,359,960 | B1 | 3/2002 | Wahl et al. | |
| 7,155,043 | B2 * | 12/2006 | Daw | 382/128 |
| 7,817,835 | B2 | 10/2010 | Fan et al. | |
| 7,835,491 | B2 | 11/2010 | Fischer et al. | |
| 2008/0187095 | A1 * | 8/2008 | Boone et al. | 378/37 |
| 2010/0256480 | A1 * | 10/2010 | Bottomley et al. | 600/411 |
| 2012/0022358 | A1 * | 1/2012 | Fischer | 600/407 |

* cited by examiner

*Primary Examiner* — Andrew W Johns
*Assistant Examiner* — Tahmina Ansari
(74) *Attorney, Agent, or Firm* — Schiff Hardin LLP

(57) ABSTRACT

In a device and associated method to extract a tissue sample, spatial coordinates of tissue variations in slice images are determined and tested by a forward projection in projection images in order, with tested spatial coordinates, to create revised slice images with a precise localization of a tissue variation.

12 Claims, 4 Drawing Sheets

Data Store
Computer
SP
RE
B
EH
RP
VM
Slice Image Generation Module
Testing Module
Needle Mount
NH
Biopsy Needle
KP
N
z
y
x
0
D
Mxy
Radiation Detector Target Selection Module
AM
Identifier Module
KMPT
Calculation Module
MVP
Comparison Module
VMTP
TOL
Marking Assignment Module
NTP
RP
Slice Image Revision Module
SUEM
VM
Testing Module

DEVICE AND METHOD TO EXTRACT A TISSUE SAMPLE

BACKGROUND OF THE INVENTION

1. Field of the Invention

The present invention concerns a method and device to assisting in the extraction of a tissue sample, i.e., to implement a biopsy.

2. Description of the Prior Art

In a biopsy a tissue sample (for example from the breast of a patient) is extracted and histologically examined. The tissue extraction for the most part takes place with the assistance of an imaging method.

One imaging method in mammography for the diagnosis of breast cancer is stereotactic imaging. For this, the breast is compressed and fixed with a compression device in a mammography apparatus. Whether the region to be examined is suitable for a diagnostic—i.e. whether it contains the lesion discovered in the clarification mammogram—is checked with a first x-ray acquisition. A second and third x-ray exposure are subsequently made from a positive and negative angle relative to the first x-ray exposure in order to calculate from these the spatial arrangement of the target, for example of a tumor or its micro-calcifications. After this the biopsy needle is introduced into the breast and the position of the biopsy needle is monitored with an additional stereo exposure.

In a further imaging method, slice images of a tomosynthesis method are used to assist in diagnostics and to determine the spatial coordinates for an extraction of a tissue sample. In tomosynthesis methods a tomosynthesis reconstruction process is applied with which a volume data set of a subject is created. The volume data set includes slice images in which tissue variations can be localized and assessed. A sequence of, for example 25 x-ray images is created to implement the tomosynthesis. For this purpose, an x-ray source is moved across a detector, for example in an angle range between +25° and −25° on a circle segment. The radiation of the x-ray source is triggered at regular intervals and an x-ray image is read out from the detector and cached. A number of slice images extending parallel to the detector and stacked along a line perpendicular to the detector are subsequently created on the basis of the x-ray exposures in a tomosynthesis method, for example. Depending on examination- and apparatus-specific limitations in the deflection of the x-ray source, a depth resolution (i.e. the resolution along the perpendicular line) is lower relative to the resolution that can be achieved horizontally. This has the disadvantage of an imprecision in the determination of the spatial coordinates for a biopsy. However, the depth resolution of tomosynthesis is still better than that of stereotaxis, so the uncertainty in the coordinate determination is also less.

SUMMARY OF THE INVENTION

An object of the invention is to provide a device and a method that further reduces the disadvantages described above.

This object is achieved in accordance with the invention by a device and an associated method for the extraction of a tissue sample, that make use of a volume set of a subject (the volume set having slice images). A tissue variation in the slice images is determined by a testing module and provided with a first marking. From the volume set, the testing module calculates projection images with the transferred first markings. After a review of the markings in the present projection images, slice images are calculated again.

The invention has the advantage that lesions can be presented more precisely in the z-direction in the slice images.

The invention has the further advantage that the spatial coordinates for a tissue extraction can be determined more exactly.

The invention has the further advantage that the scan density/number of slices—and therefore the slice interval—in a volume set that is to be newly or partially created can be varied with the determined coordinates of the tissue variation.

The invention also has the advantage that a better resolution can be achieved with additional interposed slices, for example in a region of a tissue variation that is to be considered.

The invention also has the advantage that, according to a prioritized target consideration, only a determinable number of slices in the region of a selected target are subject to a forwards/backwards projection.

The invention has the further advantage that, due to the spatial coordinate check before a new creation of a sequence of tomosynthesis projections, individual projections can be acquired with a higher x-ray radiation in order to be able to determine a better localization of a target.

The invention also has the advantage that the marking of the target for the tomosynthesis-assisted biopsy takes place both in the projection images and in the reconstructed slices.

DESCRIPTION OF THE PREFERRED EMBODIMENTS

In the device and the associated method according to the invention, spatial coordinates of tissue variations are determined in slice images and tested by means of a forward projection in projection images in order, with revised spatial coordinates, to create revised slice images with a precise locality of a tissue variation.

Figure 1:
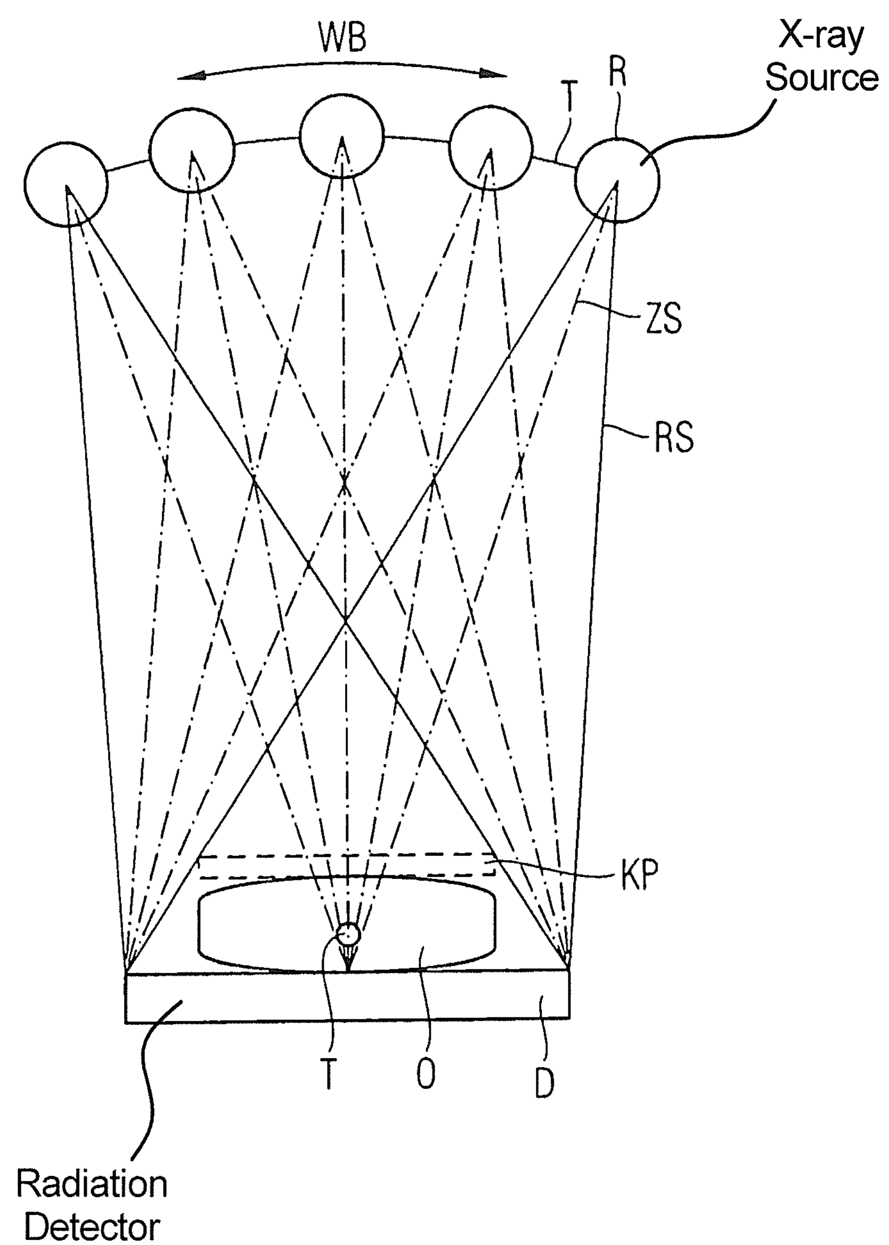
FIG. 1 illustrates a tomosynthesis scan.
Figure 5:
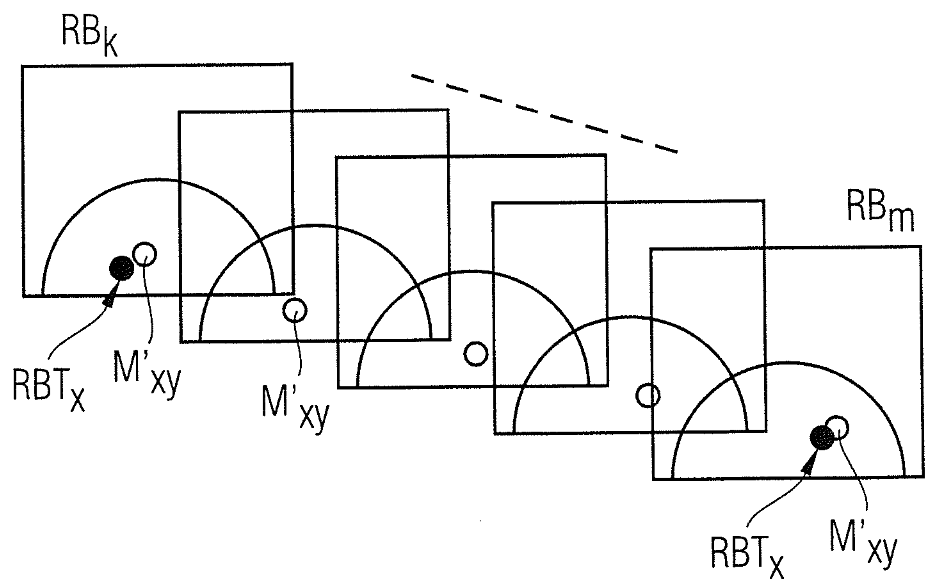
FIG. 5 shows projections after a forward projection according to the invention.

A trajectory T of an x-ray tube R of a mammography apparatus is depicted in FIG. 1. The breast O is fixed by a compression plate KP. Controlled by sensors, this compression plate KP is driven by a motor or adjusted manually. Before the x-ray acquisitions the breast O is placed on the detector surface and compressed and fixed by means of a compression unit. The entire detector region or portions of this can be exposed by means of the x-ray beam RS emanating from the x-ray source R. The central ray ZS of the x-ray beam RS can be aligned on a portion of the breast O. In FIG. 5, stations of the x-ray tube R on the trajectory T are depicted as examples. The trajectory T can proceed as shown, along a circle segment or arbitrarily within a plane. For tomosynthesis a first sequence of, for example, 25 is created. The x-ray tube R is thereby moved across the detector D along a circle segment in an angle range WB between +25° and −25°. Subjects within the breast that have different distances from the detector surface are projected on the detector surface at different points along the trajectory. During the subsequent reconstruction (for example via methods of filtered back-projection, RWP)—conspicuous tissue structures in the breast are shown enhanced in slice images via suitable filtering, shifting and addition. The reconstruction leads to a series of slice images at different depth levels parallel to the detector surface. After a prioritization, among a number of tissue variations the tomosynthesis slice or slices in which a tissue variation has an evaluable structure or peculiarity is/are determined by means of a selection algorithm. With the determination of the slice or the slices, among other things the z-coordinate and (in the slice) the x, y coordinates of the tissue variation can be determined. Due to the limited number of x-ray exposures and the size of the circle segment on which the x-ray head moves, the resolution in the z-direction is less than the slice images extending in the x, y direction.

Figure 2:
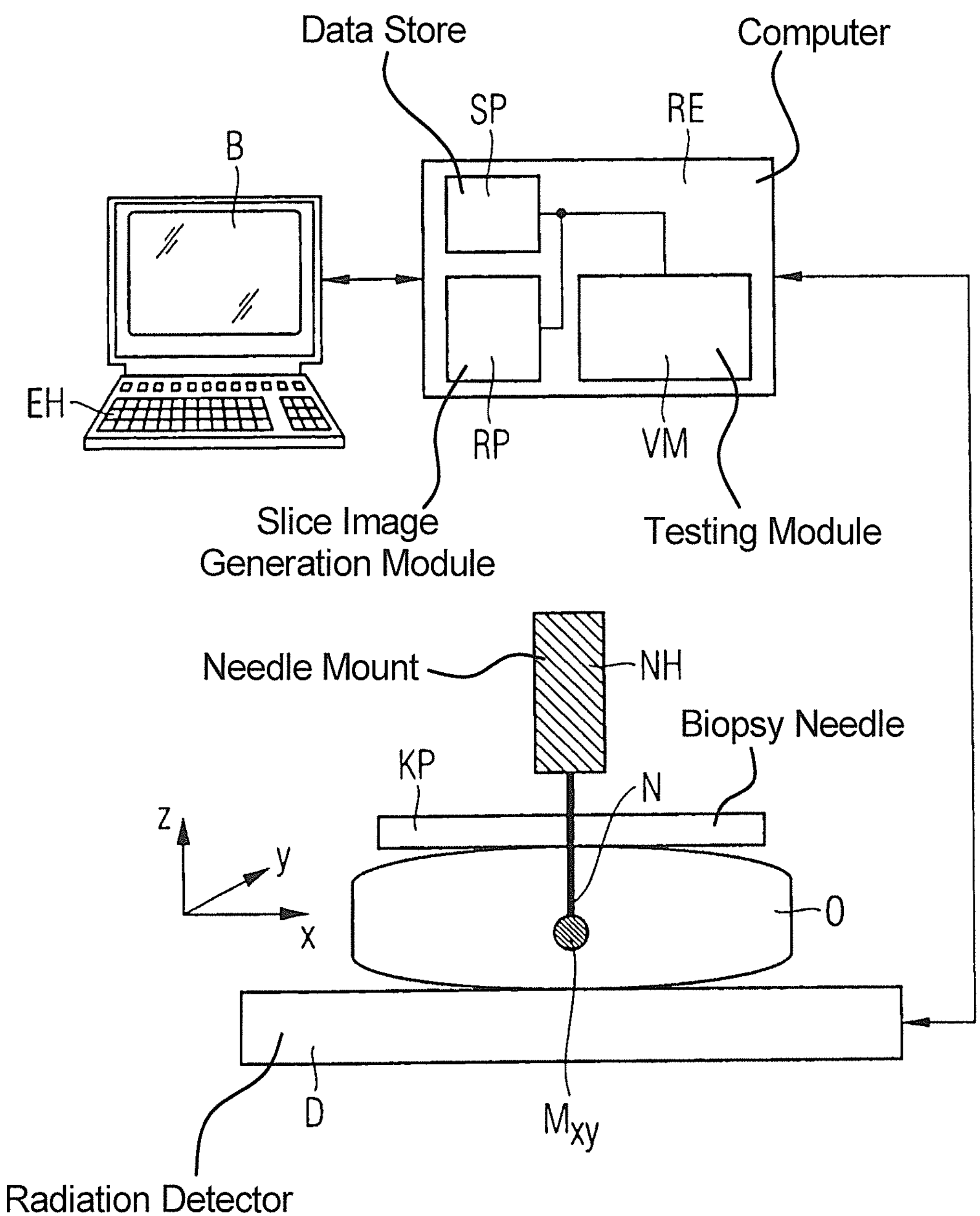
FIG. 2 shows basic components of a mammography system according to the invention.

Components of a mammography system are depicted in FIG. 2. Depicted are: components of a compression unit made up of compression plate KP and detector unit D; a needle mount NH with biopsy needle N; and a data processing unit. In this arrangement the schematically depicted data processing unit is shown with a computer RE and a monitor B. Among other things, a slice image generation module RP and a testing module VM to test spatial coordinates for a target Mxy to be examined are depicted in the computer RE. A number of x-ray exposures of the breast O are made during a scan, wherein the x-ray images are respectively read out from the detector D and cached in a data store SP of the computer RE until processing.

Figure 3:
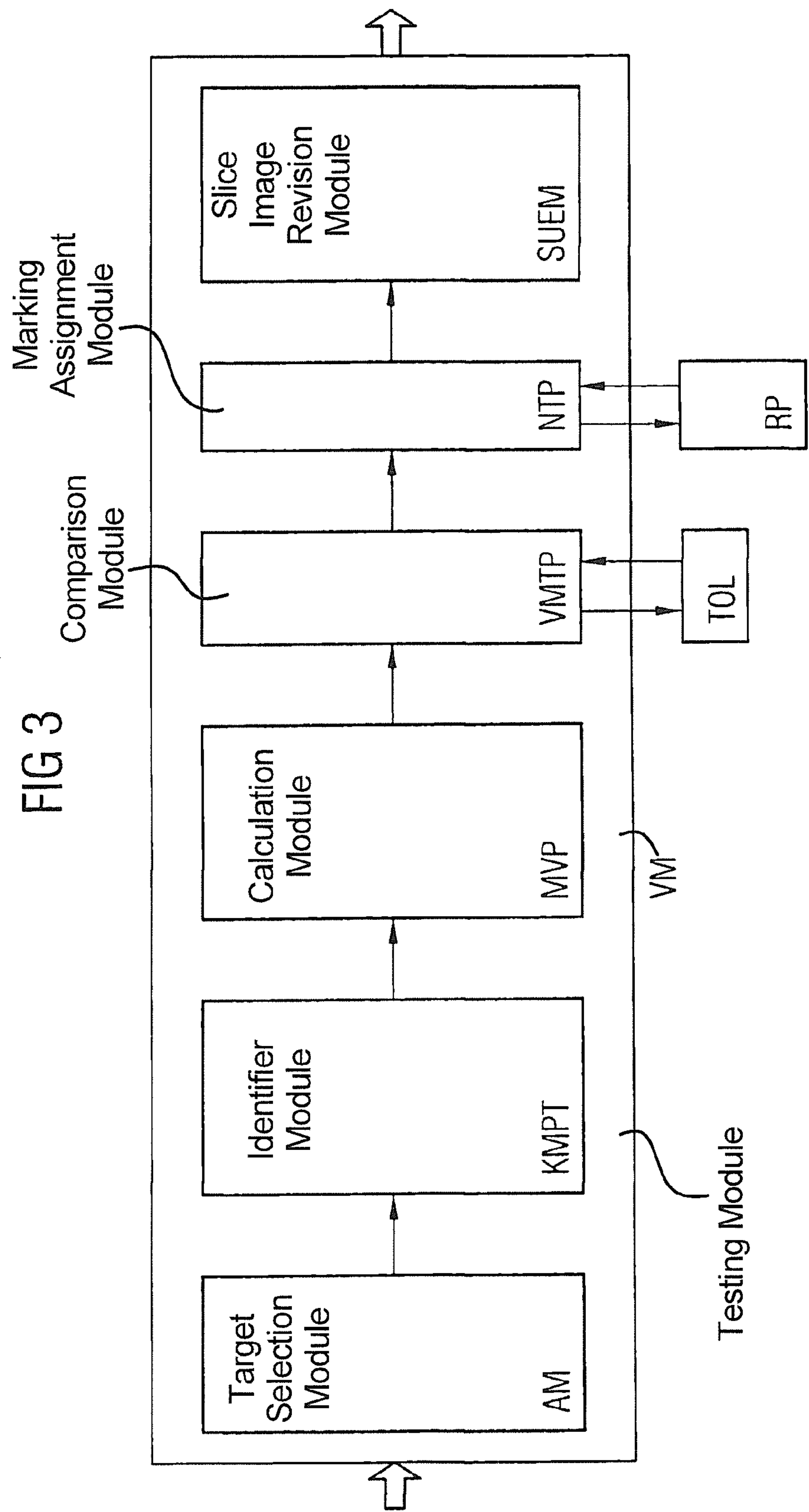
FIG. 3 illustrates a testing module according to the invention.

A testing module VM is depicted in FIG. 3 in the form of a flow chart. Among other things a target selection module MVP, an identifier module KMPT, a calculation module MVP, a comparison module VMTP, a marking assignment module NTP and a slice image revision module SUEM are arranged in the testing module VM. With the testing module VM, spatial coordinates of a target Mxy marked in a stack of slice images are analyzed in the forward projections and corrected if a predeterminable tolerance value TOL is exceeded. The shown testing module VM has a target selection module AM at the input side to select a specific target Mxy. In this target selection module AM, given a number of targets in a stack of slice images TSn, . . . , TSn+x at least one target is determined manually or as controlled by a program. In the subsequent identification module KMPT a determined target is provided with a first marking Mxy. Regions that can be biopsied are marked in the tomosynthesis slices. A selection criterion can be a significant sharpness of a suspicious structure, a lesion previously identified in the diagnostic clarification exposures, the tissue variation imaged in the slice image TSn, . . . , TSn+x. A forward projection of the slice image data including the marking Mxy subsequently takes place with the calculation algorithms integrated into the calculation module MVP. It is also possible that only the marking points are projected forwards and are subsequently inserted into the already extant, measured projections. Given a forward projection projections are calculated under consideration of the geometry of the data exposure. The image data of the projection images RBk, . . . , RBm—including the projected first marking or markings Mxy—are stored in the buffer SP of the computer RE for additional processing. At the output side, projection images RBk, . . . , RBm including the projected first marking or markings Mxy can be tapped by the computer module MVP. The first marking Mxy from the slice images is designated with "projected first marking" M'xy in the projection images RBk, . . . , RBm. Conspicuous structures in the projection images RBk, . . . , RBm, in particular in the region of the projected first marking M'xy, are selected by means of a selection algorithm and provided with a second marking RBTx if they do not coincide with the lesions visible in the projection images. The second marking RBTx can take place in multiple projection images RBk, . . . , RBm. Deviations in the target markings between the transferred first marking M'xy and the second marking RBTx are considered in the comparison module VMTP. If the deviation between the transferred first marking M'xy and the second marking RBTX exceeds a predeterminable value TOL (1 mm, for example), in the marking assignment module NTP the second marking RBTx is used for a new back-projection to be implemented in the slice image creation module RP. Given a subsequent computer-controlled evaluation of the tissue coordinates, an offset of these relative to the originally determined biopsy coordinates is displayed, for example. Based on the revised spatial coordinates, given a possible variation of the value (for example of the z-coordinate) in the considered target this is imaged more exactly in the stack of the slice images ST via additional interposed slice images. In order to minimize calculation time, for example, only the slices around the localized tissue variation could be recalculated and inserted into an existing volume set. These and continuative calculation procedures are conducted in the slice image revision module SUEM.

For presentation, the x-ray images with the marked tissue variations, the slice images calculated from these and the results of the forward projection can be presented in screen segments of a monitor or on multiple monitors.

Figure 4:
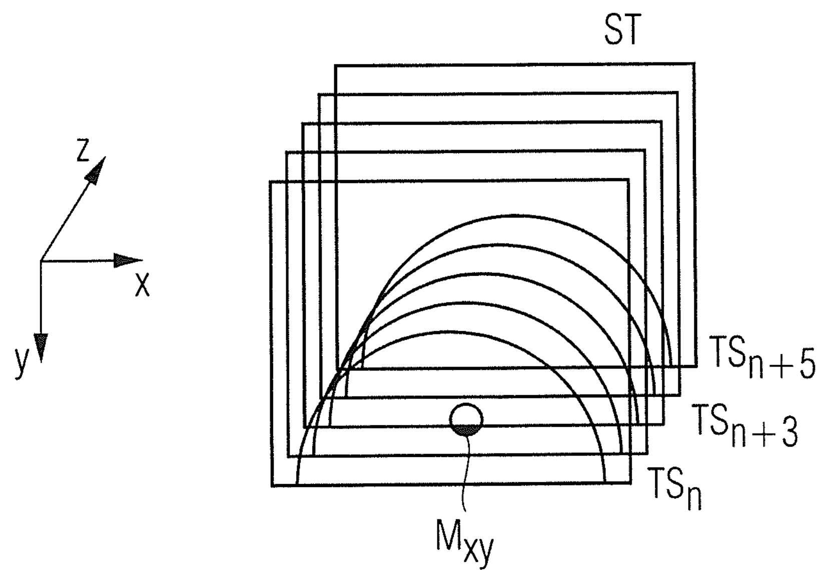
FIG. 4 shows a stack with slice images.

A low count of slice images TSn, TSn+k is depicted as an example in FIG. 4. Given a review of the individual slice images, based the structure of a target in the slice images it results that a biopsy is to be implemented for a continuative examination. The spatial coordinates of the tissue variation are checked before the tissue extraction. For a further consideration of the tissue variation this is provided with a first marking Mxy.

The x-ray images or, respectively, the projection images RBk, . . . , RBm that were calculated by means of forward projection from the data of the slice images ST are depicted in FIG. 5. The projected first marking M'xy is also depicted. A selected tissue variation RBTx is also additionally marked in the projection images RBk, . . . , RBm. As described above, one and the same tissue variation forms a basis for its marking Mxy, M'xy, RBTx. If the value of the projected first marking M'xy relative to the marking RBTx—which corresponds to the real position of the lesion (tumor position)—now exceeds a threshold TOL, the second marking RBTx is used to calculate a new/revised volume set given application of the calculation algorithms of the back projection RWP in the slice image generation module RP in the computer RE. The point RBTx in the volume data set is thereby recalculated. Since the marking RBTx can also be introduced in multiple forward-projected projections RBk, RBk+1, RBk+2, . . . , it is not guaranteed that these markings are consistent, i.e. also correspond to the same spatial point in the volume data set given reconstruction. Given multiple markings, the spatial point is estimated with an estimation method (for example least square method) that is best compatible with the individual markings RBTx. In the last step the coordinates determined in this manner are relayed to the biopsy unit to control the needle.

Although modifications and changes may be suggested by those skilled in the art, it is the intention of the inventors to embody within the patent warranted hereon all changes and modifications as reasonably and properly come within the scope of their contribution to the art.

We claim as our invention:

1. A device to assist in extraction of a tissue sample from a subject, comprising:

a computerized processor having an input supplied with a volume data set representing a plurality of acquired slice images acquired from an examination subject with an x-ray source and a radiation detector, said acquired slice images forming a stack of acquired slice images in respective slices of the subject parallel to said radiation detector;

said processor being configured to identify a tissue variation in said acquired slice images and to indicate said tissue variation in the acquired slice images with a first marking;

said processor being configured to execute a first image reconstruction algorithm to calculate projection images, with said first marking projected therein, from the acquired slice images with the first marking therein;

said processor being configured to execute a second image reconstruction algorithm to calculate calculated slice images from said projection images that include a representation therein of the projected first marking in said projected images, as a calculated second marking that results from application of said second reconstruction algorithm to said first marking projected in said projection images; and said processor being configured to determine biopsy coordinates that coincide with said calculated second marking in the calculated slice images and to provide said biopsy coordinates at an output of said processor in a form allowing a tissue sample to be extracted from the examination subject at a location corresponding to said biopsy coordinates.

2. A device as claimed in claim 1 wherein said processor comprises a computerized comparison unit configured to compare coordinates of said first marking in said projection images with coordinates of said calculated second marking in the calculated slice images to identify a difference therebetween, and wherein said processor is configured to implement a verified slice image calculation if said difference exceeds a predetermined value.

3. A device as claimed in claim 1 comprising a display in communication with said processor, and wherein said processor is configured to cause said calculated slice images to be displayed at said display with a visual representation of said calculated second marking.

4. A device as claimed in claim 3 wherein said processor is configured to interpose a plurality of calculated slices in a region of said calculated second marking in said display.

5. A device as claimed in claim 1 wherein said processor is configured to calculate said projection images from the acquired slice images by implementing a forward projection of said acquired slice images, as said first reconstruction algorithm.

6. A method to assist in extraction of a tissue sample from a subject, comprising:

supplying a computerized processor with a volume data set representing a plurality of acquired slice images acquired from an examination subject with an x-ray source and a radiation detector, said acquired slice images forming a stack of acquired slice images in respective slices of the subject parallel to said radiation detector;

in said processor, identifying a tissue variation in said acquired slice images and indicating said tissue variation in the acquired slice images with a first marking;

in said processor, calculating projection images, with said first marking projected therein, from the acquired slice images with the first marking therein, by executing a first reconstruction algorithm;

in said processor, executing a second reconstruction algorithm to calculate slice images from said projection images that include a representation therein of the projected first marking in said projected images, as a calculated second marking that results from application of said second reconstruction algorithm to said first marking projected in said projection images; and in said processor, determining biopsy coordinates that coincide with said calculated second marking in the calculated slice images and providing said biopsy coordinates at an output of said processor in a form allowing a tissue sample to be extracted from the examination subject at a location corresponding to said biopsy coordinates.

7. A method as claimed in claim 6 comprising, in said processor, comparing coordinates of said first marking in said projection images with coordinates of said calculated second marking in the calculated slice images to identify a difference therebetween and, in said processor, implementing a verified slice image calculation if said difference exceeds a predetermined value.

8. A method as claimed in claim 6 comprising, from said processor, causing said calculated slice images to be displayed at said display with a visual representation of said calculated second marking.

9. A method as claimed in claim 8 comprising, from said processor, interposing a plurality of calculated slices in a region of said calculated second marking in said display.

10. A method as claimed in claim 6 comprising, in said processor, calculating said projection images from the acquired slice images by implementing a forward projection of said acquired slice images as said first reconstruction algorithm.

11. A method as claimed in claim 10 comprising, in said processor, calculating said calculated slice images from said projection images by implementing a backward projection of said projection images, as said second reconstruction algorithm.

12. A device as claimed in claim 5 wherein said processor is configured to calculate said calculated slice images from the projection images by implementing a backward projection of said projection images, as said second reconstruction algorithm.

* * * * *